United States Patent [19]

Steiner

[11] Patent Number: 4,976,968
[45] Date of Patent: Dec. 11, 1990

[54] ANHYDROUS DELIVERY SYSTEMS FOR PHARMACOLOGICAL AGENTS

[75] Inventor: Solomon S. Steiner, Mt. Kisco, N.Y.

[73] Assignee: Clinical Technologies Associates, Inc., Elmsford, N.Y.

[21] Appl. No.: 315,440

[22] Filed: Feb. 24, 1989

[51] Int. Cl.$^5$ .............................................. A61K 9/50
[52] U.S. Cl. ..................................... 424/491; 424/455
[58] Field of Search .................... 530/841, 813, 812; 424/95, 450, 491, 455; 514/21, 869

[56] References Cited

U.S. PATENT DOCUMENTS

| | | | |
|---|---|---|---|
| 3,052,655 | 9/1962 | Fox et al. | 260/78 |
| 3,076,790 | 2/1963 | Fox et al. | 260/78 |
| 3,576,758 | 4/1971 | Emrick | 252/316 |
| 3,794,561 | 2/1974 | Matsukawa et al. | 530/841 |
| 3,822,348 | 7/1974 | Higashi et al. | 424/95 |
| 3,962,416 | 6/1976 | Katzen | 426/103 X |
| 4,061,466 | 12/1977 | Sjohölm et al. | 530/813 X |
| 4,217,370 | 8/1980 | Rawlings | 426/98 |
| 4,272,506 | 6/1981 | Schwarzberg | 530/813 X |
| 4,351,337 | 9/1982 | Sidman | 128/260 |
| 4,388,304 | 6/1983 | Nyéki et al. | 530/800 X |
| 4,492,684 | 1/1985 | Goosen et al. | 424/19 |
| 4,647,455 | 3/1987 | De Bold | 514/869 X |
| 4,671,954 | 6/1987 | Goldberg et al. | 424/450 |
| 4,703,042 | 10/1987 | Bodor | 514/822 X |
| 4,753,804 | 6/1988 | Iaccheri et al. | 424/499 |
| 4,757,024 | 7/1988 | Roper | 530/812 X |
| 4,774,320 | 9/1988 | Tagliabue et al. | 530/328 |
| 4,789,734 | 12/1988 | Pierschbacher | 530/841 X |
| 4,844,904 | 7/1989 | Hamaguchi et al. | 424/450 |

FOREIGN PATENT DOCUMENTS

| | | |
|---|---|---|
| 78300208.2 | 2/1979 | European Pat. Off. |
| 2424169 | 12/1974 | Fed. Rep. of Germany |
| 2565102 | 6/1984 | France |
| 58-035111 | 3/1983 | Japan |

OTHER PUBLICATIONS

Przybylski and Fox, *Appl. Biochem. Biotech.* 10, 301–307 (1964).
Matsuno, *BioSystems* 17, 11–14 (1984).
Kokufuta, et al., *BioSystems* 16, 175–181 (1984).
Sun et al., *Chemical Abstracts* 105:12027p (Pharmaceuticals, vol. 105, 1986).

*Primary Examiner*—Thurman K. Page
*Attorney, Agent, or Firm*—Kilpatrick & Cody

[57] ABSTRACT

Substantially anhydrous pharmacological agents microencapsulated within protective hollow proteinoid microspheres are produced by contacting an aqueous mixture of such agent with an insoluble proteinoid and lyophilizing the resulting microspheres. Such encapsulation and dehydration results in a free flowing powder that has a long shelf life under naturally occurring temperature conditions and that quickly reabsorbs water without damage to the capsular wall. Gastrointestinally labile or poorly absorbed agents, such as insulin, heparin or dopamine redox carrier system, which are so microencapsulated in protective microspheres are rapidly rehydrated by body fluids in the gastrointestinal tract. Those microspheres having a diameter of about 10 microns or less penetrate the gastrointestinal mucosa and release the agent into the bloodstream in physiologically active form.

20 Claims, No Drawings

ANHYDROUS DELIVERY SYSTEMS FOR PHARMACOLOGICAL AGENTS

BACKGROUND OF THE INVENTION

1. Field of the Invention

This invention relates to substantially anhydrous pharmacologically active agents which are protectively microencapsulated within proteinoid microspheres and to their preparation. It relates particularly to the oral administration of dehydrated microspheres encapsulating biologically active agents, such as polypeptides, which otherwise would be labile in storage and poorly absorbed from the gastrointestinal tract.

2. Description of the Prior Art

The available modes of delivery of pharmaceutical and therapeutic agents often are severely limited by chemical or physical barriers or both, which are imposed by the body. For example, oral delivery of many such agents would be the general method of choice if not for the numerous barriers faced by these agents along this route. Gastrointestinal conditions of inappropriate pH, the presence of powerful digestive enzymes, the permeability properties of gastrointestinal membranes and tissues and other factors all play important roles in determining the feasibility of oral delivery of active agents to their targets. Among the numerous pharmacological agents which are known to be adversely affected or rendered ineffective when administered orally are the biologically active polypeptides and proteins, such as insulin, and mucopolysaccharides, such as heparin. These agents are rapidly destroyed in the stomach by acid hydrolysis and in the stomach and lower gastrointestinal tract by enzymes and, in addition, they pass poorly, if at all, through the gastrointestinal mucosa.

A great deal of effort has been concentrated on the modification or isolation of the deleterious conditions within the gastrointestinal tract so that a pharmacological agent, which otherwise would be labile, could be absorbed through the stomach or intestine wall intact and in pharmacologically active form.

Copending application Ser. No. 98,027 issued as U.S. Pat. No. 4,925,673, the disclosure of which is incorporated herein by reference, teaches that hollow acidic, basic and neutral proteinoid microspheres form spontaneously in and encapsulate acidic, basic and neutral aqueous environments, respectively, and, being stable in those environments, effectively isolate and protect a pharmacological agent encapsulated therein. It also teaches that the agent can be quickly released in pharmacologically active form merely by a change in pH which causes the microspheres to lose their protective structural integrity and that such microspheres that have a diameter of less than about 10 microns readily penetrate the gastrointestinal mucosa.

More specifically, application Ser. No. 98.027 issued as U.S. Pat. No. 4,925,673 teaches that contacting an acidic proteinoid with an acidic aqueous solution or suspension of a pharmacological agent which is stable in such solution or suspension results in the spontaneous formation of hollow proteinoid microspheres encapsulating the pharmacological agent. These microspheres, being stable to stomach acids and enzymes, protect an encapsulated pharmacological agent from those acids and enzymes. Such microspheres having a diameter of less than about 10 microns readily penetrate the gastrointestinal mucosa and enter a higher pH environment where the acidic proteinoid capsule material is unstable and releases the pharmacological agent in physiologically active form into the near neutral blood stream.

It also teaches how to encapsulate within basic proteinoid microspheres pharmacological agents which are sensitive to the conditions of encapsulation within acidic proteinoid microspheres. Such microcapsules form spontaneously when the basic proteinoid is contacted with a basic aqueous solution or suspension of that pharmacological agent. The resulting microspheres are stable in the mildly basic portions of the lower digestive tract, thereby protecting the encapsulated agent from intestinal enzymes. As in the case of the acidic microspheres, basic proteinoid microspheres having a diameter of less than about 10 microns will readily penetrate the gastrointestinal mucosa into a lower pH environment where the capsule material is unstable and releases the active pharmacological agent in the near neutral blood.

Ser. No. 98.027 issued as U.S. Pat. No. 4,925,673 further teaches how to encapsulate a pharmacological agent within neutral proteinoid microspheres by contacting neutral proteinoid with a neutral aqueous solution or suspension of that agent. Such microspheres are stable in the near neutral bloodstream and release the active agent in response to higher or lower pH at which these microspheres are unstable.

Ser. No. 98,027 issued as U.S. Pat. No. 4,925,673 thus provides an effective means for targeting the release of a pharmacologically active agent in an animal by incorporating same in proteinoid microspheres which are stable to the conditions encountered during migration from the point of introduction into the animal to a targeted release zone where they are unstable. However, the water content of such microspheres often leads to an undesirably short shelf life or storage stability.

Since the microspheres can be punctured by the large ice crystals which form during natural freezing, it is essential that they be protected from such conditions during both shipment and storage. In addition, the presence of water in contact with many pharmacological agents results in the progressive hydrolysis of chemical bonds and degradation of the biological activity. In the case of insulin and other biologically active polypeptides, this degradation is quite rapid. For example, although Ser. No. 98,027 issued as U.S. Pat. No. 4,925,673 shows that the unrefrigerated shelf life of aqueous insulin can be dramatically lengthened by encapsulation within acidic proteinoid microspheres, that shelf life is measured only in weeks. Still another problem is introduced by the fact that it is exceedingly difficult to isolate the microspheres from a wide variety of microorganisms, including certain molds having air borne spores, which are capable, in a aqueous environment, of utilizing the proteinoid as a nutrient. Such microorganisms also can similarly attack and destroy insulin, as well as other polypeptides, proteins and certain polysaccharides.

Since dehydration has long been known to enhance the shelf life of many unencapsulated pharmacological agents, including insulin (the effectiveness of which can be extended for several months), efforts have been made to dehydrate orally administerable acidic proteinoid microspheres containing aqueous insulin by vacuum drying at room or slightly elevated temperatures. Although this procedure dehydrates the insulin, the pressure drop across the proteinoid capsular walls resulting from the egress of liquid water ruptures those walls and exposes the dehydrated insulin, thereby rendering the composition unsuited for oral administration.

SUMMARY OF THE INVENTION

It is an object of this invention to provide a means for dehydrating an aqueous pharmacological agent which is encapsulated within proteinoid microspheres without rupturing the proteinoid capsular walls. It is a further object to provide such substantially anhydrous agent encapsulated within hollow proteinoid microspheres and, thereby, to extend the storage stability of such agent. It is still another object to provide such microencapsulated dehydrated agent in free flowing powder form to facilitate the preparation of factory packaged unit dosages having extended shelf life.

It has been found that these objects and other advantages, which will be apparent from this specification, are achieved by the invention described below.

It now has been found that an aqueous solution or suspension of a pharmacological agent encapsulated within hollow proteinoid microspheres, as described in Ser. No. 98,027 issued as U.S. Pat. No. 4,925,673, can be rendered substantially anhydrous without rupturing the capsular walls by lyophilization; i.e., by flash freezing those microspheres and then dehydrating them by sublimation of the microcrystalline ice. Pharmacological agents which are encapsulated and dehydrated in this manner exhibit an unrefrigerated shelf life which is far in excess of that of similar aqueous microspheres. These dehydrated microspheres, being stable under normally occurring temperature conditions, require no thermal protection during shipment or storage.

It also has been found that such dehydrated pharmacological agents become totally rehydrated within a few seconds when the microspheres are contacted with water that is pH adjusted to be a non-solvent for the proteinoid or with body fluids of similar pH. Surprisingly, the capsular walls remain intact in spite of this very rapid entry of water into the microcapsules. This unexpected retention of protective capsular walls during rapid rehydration by body fluids, coupled with the the fact that the dehydrated microspheres are an easily measured free flowing powder, facilitates the preparation and administration of anhydrous unit dosages which are packaged under factory conditions that exclude the deletereous effects of microorganisms and water.

DESCRIPTION OF PREFERRED EMBODIMENTS

Lyophilization has been found to be an effective means for dehydrating any aqueous pharmacologically active agent which is microencapsulated within acidic, basic or neutral proteinoid microspheres, as taught by Ser. No. 98.027 issued as U.S. Pat. No. 4,925,673. These microencapsulated aqueous agents conveniently are made simply by contacting the selected proteinoid with an aqueous solution or suspension of the active agent which is pH adjusted to be a non-solvent for that proteinoid. The preferred proteinoid materials for use in preparing such microencapsulated aqueous agents are thermal condensation polymers derived from at least one acidic or basic amino acid and at least one other acidic, basic or neutral amino acid. Although microsphere forming polymers can be derived from as few as two such amino acids, a greater diversity generally results in higher yields of uniform size microspheres. Proteinoids derived from only the D, L or DL forms of naturally occurring amino acids (i.e., those found in animal or vegetable protein) are greatly preferred as it has been shown that when such proteinoids dissolve in human serum or in the bloodstreams of rats or guinea pigs, they consistently break into low molecular weight fragments which produce no detectable toxic or immunological response. This desirable characteristic is unaffected by lyophilization, even after prolonged storage, indicating that the chemical structure of the proteinoid is not altered by this dehydrating technique.

The dehydrated microspheres of this invention exhibit the same pH sensitive solubility characteristics as their aqueous precursors and have the same utility.

For example, lyophilized acidic proteinoid microspheres are gastrically stable and dissolve rapidly at the near neutral pH of blood. Those microspheres having a diameter of less than about 10 microns readily penetrate the gastrointestinal mucosa and are particularly well suited for the oral administration and delivery to the bloodstream of biologically active proteins and polypeptides, such as insulin, ANF, calcitonin, EPO, CGSF, bovine or human growth hormone and hepatitis B, rubella, diphtheria and whooping cough vaccines, as well as mucopolysaccharides, such as heparin, and antibiotics, such as certain cephalosporins or piperacillan, which otherwise must be administered parenterally.

Lyophilized basic proteinoid microspheres are stable in the weakly basic portions of the lower gastrointestinal tract and also dissolve rapidly at the near neutral pH of the blood. Those microspheres having a diameter of less than about 10 microns readily penetrate the gastrointestinal mucosa and are particularly well suited for administration to those weakly basic regions and delivery to the bloodstream of redox carriers for dopamine, gamma aminobutyric acid and other biologically active agents which otherwise would not penetrate the brain/blood barrier.

Lyophilized neutral proteinoid microspheres are stable in the near neutral blood serum and dissolve at higher pH, such as that encountered when engulfed within macrophages. Such microspheres, which desirably are rehydrated outside the animal body, are suited for the intravenous administration of azidothymidine, the interferons, peptide T or ribovaran.

Example 1 illustrates an especially preferred method of producing high yields of gastrically stable dehydrated polypeptide bearing acidic proteinoid microspheres which quickly absorb water, readily penetrate the gastrointestinal mucosa and are soluble at the near neutral pH of the blood.

EXAMPLE 1a

A flask equipped with an electric heating mantle and containing equimolar quanties of anhydrous aspartic acid, glutamic acid, valine and glycine is heated at approximately 175° C. under a stream of nitrogen until the contents are molten. The nitrogen swept mixture then is agitated gently with a glass encased magnetic stirrer and the temperature is raised to and held at 180° C. for six hours. After cooling, the dark amber product is extracted with saturated aqueous sodium bicarbonate and the extract dialyzed through a collodion membrane against distilled water at room temperature for 24 hours, the water being changed every four hours. The entire content of the dialysis tubes then is dried under vacuum at 65° and the residual solids are ground to a fine powder with mortar and pestle.

EXAMPLE 1b

An aqueous solution of proteinoid is produced by mixing 35 mg of the powder of Example 1a per ml of water, adjusting the pH to 7.4 with concentrated aqueous sodium bicarbonate and removing any insoluble materials by filtration. One part by volume of this solids free solution of proteinoid then is rapidly injected into an equal volume of a freshly prepared 25 mg/ml mixture of porcine insulin in pH 2.25 aqueous acetic acid. The mixture, which has a pH of approximately 3.5, is stirred in an ice bath for 15 minutes and filtered to separate the insulin bearing microspheres from the filtrate which is discarded. After washing twice with pH 3.5 aqueous acetic acid, the microspheres are resuspended in 10 parts by volume of pH 3.5 aqueous acetic acid. Microscopic examination of a portion of this suspension shows a high yield of microspheres which are predominantly between 0.5 and 5.0 microns in diameter and which dissolve rapidly when the suspension is neutralized to pH 7.4 by the addition of concentrated aqueous sodium bicarbonate. The pH 3.5 aqueous acetic acid suspension of microspheres is stored in a closed jar at room temperature.

EXAMPLE 1c

One liter of the freshly prepared pH 3.5 aqueous acetic acid suspension of microspheres of Example 1b is lyophilized in a Vir Tio model M248633 Freezemobile utilizing a dry ice/acetone bath and overnight drying under a vacuum of about 0.02 mm Hg to yield a substantially anhydrous free flowing powder. Microscopic examination of the powder product shows the microspheres to be intact. Seven equal weight samples of this powder are placed in separate sealed vials and stored at room temperature.

EXAMPLE 2

The powdered dehydrated microspheres contained in one of the storage vials of Example 1c are rehydrated by adding them to pH 3.5 aqueous acetic acid. Microscopic examination of the resulting suspension immediately after rehydration and after 24 hours storage at room temperature reveals that the microspheres remain intact and are visually indistinguishable from those in the pH 3.5 aqueous acetic acid suspension of Example 1b. This rehydrated sample and a sample of the suspension of Example 1b each is neutralized to pH 7.4 with saturated aqueous sodium bicarbonate and the microspheres of each are observed to dissolve at the same rapid rate.

EXAMPLE 3

Within 24 hours after lyophilization, the powdered dehydrated microspheres of a second storage vial of Example 1c are rehydrated by adding them to 15 ml of pH 3.5 aqueous acetic acid. A one ml dose of the resulting suspension is administered by gavage to each of 10 arbitrarily selected young male rats weighing approximately 500 g and having normal blood glucose levels. Blood samples are withdrawn from the tails immediately before dosage and at half hour intervals thereafter for 24 hours. The maximum percentage reduction of blood glucose and the duration of the effect in the animals are averaged to provide baseline figures.

EXAMPLE 4

The procedure of Example 3 is repeated monthly for five additional months using the remaining vials of dehydrated microspheres of Example 1c. No significant deviation from the baseline figures is observed over the entire six month period.

It should be noted that in contrast to these results, aging of similar insulin bearing microspheres which are stored in aqueous suspension at room temperature results in a rapidly accelerating decline in effectiveness.

Example 5 illustrates a method for producing a dehydrated, acid sensitive pharmacological agent encapsulated within basic proteinoid microspheres which are stable in the weakly basic portions of the lower digestive tract, quickly absorb water, readily penetrate the gastrointestinal mucosa and are soluble at the near neutral pH of the blood. The acid sensitive agent, PR-21, is a proprietery composition of acylated dopamine bonded to a reduced dihydropyridine/pyridinium salt type redox carrier which was developed by Pharmatek, Inc. and is described in U.S. Pat. No. 4,479,932. The unprotected PR-21 composition is unstable anywhere in the gastro-intestinal tract and is particularly sensitive to acid conditions. When injected intravenously into rats, significant amounts of the deacylated quaternary precursor of dopamine can be measured in the homogenized rat brain by the method of Bodir and Farog, Journal of Medicinal Chemistry, 26 528 (1983).

EXAMPLE 5a

A nitrogen swept mixture of two parts by weight of arginine, two parts by weight of lysine and one part by weight of an equimolar mixture of the sixteen neutral and acidic aminoacids found in animal protein is stirred and heated at 180° C. for 3 hours. The cooled reaction mixture is extracted with pH 2.25 aqueous acetic acid and the extract is dialyzed through a collodion membrane against a large volume of distilled water at room temperature for 48 hours, the water being changed every six hours. The content of the dialysis tubes then is heated under vacuum at 65° C. to yield a dry powdered basic proteinoid. When suspended in a moderate to strongly alkaline aqueous environment, this powdered proteinoid spontaneously forms hollow microspheres which are stable in that environment, but which dissolve at the near neutral pH of blood.

EXAMPLE 5b

One part by volume of an ethanol solution of PR-21 (360 mg/ml) is diluted with an equal volume of distilled water and the pH of the solution is adjusted to 8 by the addition of saturated aqueous monobasic potassium phosphate buffer. This buffered solution is referred to below as unprotected PR-21.

EXAMPLE 5c

Unprotected PR-21 then is mixed with 25 mg/ml of the dry powdered proteinoid of Example 5a and chilled in an ice bath until microspheres have formed. Microscopic examination reveals that they are predominantly 0.1 to 5.0 microns in diameter. One volume of this suspension of microspheres is lyophilized by the method of Example 1c and the dehydrated powder product is stored is a sealed vial at room temperature for six months. The powder then is rehydrated by being added to one volume of aqueous ethanol solution which has been adjusted to pH 8 with saturated aqueous monobasic potassium phosphate buffer. This suspension is referred to below as rehydrated microcapsules.

EXAMPLE 6

Four normal male rats, each weighing about 500 g, are arbitrarily divided into two groups. Each of the animals is anesthetized, the jejunum is externalized and the sphincter is tied off to prevent backwash into the stomach. Two ml of unprotected PR-21, which has been freshly prepared by the method of Example 5b, is injected into the jejunum of each animal of group A and each of the group B animals similarly receives 2 ml of rehydrated microcapsules of Example 5c. One hour after dosage, the animals are sacrificed and measurements are made of the amount of deacylated quaternary precursor of dopamine in their homogenized brains. While substantial amounts are detected in the group B animals, none is found in those of group A.

Any of the lyophilized drug bearing proteinoid microspheres of this invention can be quickly rehydrated befor administration by contact with water which is pH adjusted to be a non-solvent for the proteinoid, as illustrated by the foregoing examples. However, acidic and basic proteinoid microspheres, which are stable in the stomach and weakly basic lower digestive tract, respectively, are advantageously administered to large mammals as sterile, factory prepared unit doses of anhydrous microspheres contained within a conventional nonaqueous matrix which releases the microspheres in a segment of the gastrointestinal tract in which those microspheres are stable. Upon such release, the microspheres are quickly rehydrated by body fluids.

For example, orally administerable unit doses of anhydrous drug bearing acidic proteinoid microspheres, along with optional fillers such as sugar, corn starch, gum accacia or diatomaceous earth, can easily be incorporated in conventional gelatin or synthetic polymer capsules or in sugar, edible gum or gelatin tablets which melt or dissolve in the stomach. Such acidic proteinoid microspheres also can conveniently be incorporated in liquid carriers, such as vegetable oils.

Similarly, unit doses of lyophilized drug bearing basic proteinoid microspheres for administration to the mildly basic portions of the lower digestive tract can be incorporated in conventional gelatin, wax or synthetic polymer suppositories which melt or dissolve in the rectum or large intestine. They also can be administered orally when incorporated in tablets made of such meltable or dissolvable material which have an enteric coating of a material, such as cellulose acetate phthalate or shellac, which does not dissolve until the tablet reaches that lower portion of the digestive tract.

The following example illustrates the preparation of one such unit dosage.

EXAMPLE 7

A pH 4.5 aqueous acetic acid suspension of acidic proteinoid microspheres encapsulating heparin are prepared by the method of Example 8a of Ser. No. 98,027 issued as U.S. Pat. No. 4,925,673. This suspension then is lyophilized by the method of the above Example 1c. Two piece telescoping gelatin capsules containing unit dosages suitable for a large mammal are prepared by filling each capsule with a mixture of powdered sucrose and 250 mg of the powdered dehydrated microsphere product. After storage in a sealed vial for six months at temperatures simulating natural outdoor variability (i.e., from $-10°$ C. to 33PtoPtC), the capsules are dissolved in pH 3.5 aqueous HCl at 37° C. Microscopic examination of the rehydrated microspheres shows that they are visually indistinguishable from similar freshly prepared microspheres which have not been lyophilized. They also exhibit the same rate of dissolution as such freshly prepared microspheres when the pH of the suspension is neutralized to 7.4 and, when administered by gavage to rats, there is no detectable diminution in their effectiveness in reducing blood coagulation time.

It will be apparent to those of ordinary skill in the art that numerous changes and modifications can be made in the illustrative embodiments of the invention described above without departing from the spirit or scope of the invention as set forth in the following claims.

I claim:

1. Composition comprising a substantially anhydrous biologically active pharmacological agent encapsulated within hollow proteinoid microspheres formed from thermal condensation polymers of mixed amino acids.

2. Composition of claim 1 wherein said microspheres are predominantly less than about 10 microns in diameter.

3. Composition of claim 2 wherein said microspheres are stable in at least a segment of the gastrointestinal tract, are unstable at the near neutral pH of the blood and are predominantly from about 0.1 to about 5.0 microns in diameter so as to readily penetrate the gastrointestinal mucosa and release said agent in the blood stream in physiologically active form.

4. Composition of claim 3 wherein said proteinoid is acidic and said microspheres are stable in the stomach.

5. Composition of claim 4 wherein said agent is a biologically active protein or polypeptide.

6. Composition of claim 4 wherein said agent is a biologically active mucopolysaccharide.

7. Composition of claim 3 wherein said proteinoid is basic and said microspheres are stable in the weakly basic portions of the lower digestive tract.

8. Composition of claim 2 wherein said proteinoid is neutral and said microspheres are from about 0.1 to about 5.0 microns in diameter and are stable in the near neutral bloodstream and unstable at higher or lower pH.

9. Process for dehydrating an aqueous biologically active pharmacological agent encapsulated within hollow proteinoid microspheres formed from thermal condensation polymers of mixed amino acids comprising lyophilizing said microspheres.

10. Process of claim 9 wherein said aqueous pharmacological agent is encapsulated for targeted release within a selected pH range by forming an aqueous mixture of said agent with a proteinoid that is insoluble in said mixture, said mixture having a pH outside said selected range and said proteinoid being soluble within said selected range.

11. Process of claim 10 including the preliminary purification of said proteinoid by mixing with water having a pH within said selected range and separating the resulting aqueous proteinoid solution from any insoluble material.

12. Process of claim 11 comprising
(a) forming a first aqueous mixture of said agent, said first aqueous mixture having a pH outside said selected range,
(b) forming an aqueous solution of said proteinoid by mixing said proteinoid with water having a pH within said selected range and removing any insoluble material,
(c) forming a second aqueous mixture by contacting said first mixture with said aqueous solution of proteinoid, said proteinoid being insoluble in said second mixture, (d) recovering the resulting hollow proteinoid microspheres containing said aqueous agent and (e) lyophilizing said microspheres.

13. Enterically administerable composition for delivering a pharmacological agent in physiologically active form to the bloodstream of an animal comprising a pharmacologically acceptable non-aqueous matrix containing said biologically active agent microencapsulated within hollow proteinoid microspheres formed from thermal condensation polymers of mixed amino acids having diameters of from about 0.1 to about 5.0 microns, said agent being substantially anhydrous, said matrix being unstable in at least a portion of the gastrointestinal tract and said microspheres being stable in said portion of the gastrointestinal tract and unstable at the near neutral pH of the blood.

14. Composition of claim 13 wherein a unit dosage of said agent is microencapsulated within basic proteinoid microspheres which are stable in the weakly basic portion of the lower digestive tract and said matrix is unstable in said weakly basic lower digestive tract.

15. Composition of claim 14 wherein said agent is a dopamine redox carrier system.

16. Orally administerable composition of claim 13 wherein a unit dosage of said agent is microencapsulated within acidic proteinoid microspheres which are gastrically stable and said matrix is gastrically unstable.

17. Composition of claim 16 wherein said pharmacological agent is a biologically active protein or polypeptide.

18. Composition of claim 17 wherein said pharmacological agent is insulin.

19. Composition of claim 16 wherein said pharmacological agent is a biologically active mucopolysaccharide.

20. Composition of claim 19 wherein said pharmacological agent is heparin.

* * * * *